US011767352B2

(12) United States Patent
Platten et al.

(10) Patent No.: US 11,767,352 B2
(45) Date of Patent: Sep. 26, 2023

(54) HISTONE ANTI-CANCER VACCINES

(71) Applicant: DEUTSCHES KREBSFORSCHUNGSZENTRUM, Heidelberg (DE)

(72) Inventors: Michael Platten, Heidelberg (DE); Theresa Bunse, Heidelberg (DE); Wolfgang Wick, Heidelberg (DE); Katharina Ochs, Heidelberg (DE); Martina Ott, Heidelberg (DE); Lukas Bunse, Heidelberg (DE)

(73) Assignee: DEUTSCHES KREBSFORSCHUNGSZENTRUM, Heidelberg (DE)

( * ) Notice: Subject to any disclaimer, the term of this patent is extended or adjusted under 35 U.S.C. 154(b) by 491 days.

(21) Appl. No.: 16/832,465

(22) Filed: Mar. 27, 2020

(65) Prior Publication Data
US 2020/0377562 A1 Dec. 3, 2020

Related U.S. Application Data

(63) Continuation of application No. 15/735,046, filed as application No. PCT/EP2016/066563 on Jul. 12, 2016, now abandoned.

(30) Foreign Application Priority Data

Jul. 15, 2015 (EP) .................... 15176879

(51) Int. Cl.
| | |
|---|---|
| A61K 38/16 | (2006.01) |
| A61K 38/00 | (2006.01) |
| A61P 35/00 | (2006.01) |
| C07K 14/47 | (2006.01) |
| A61K 39/00 | (2006.01) |
| C07K 14/725 | (2006.01) |
| G01N 33/574 | (2006.01) |

(52) U.S. Cl.
CPC .............. *C07K 14/47* (2013.01); *A61K 38/16* (2013.01); *A61K 39/0011* (2013.01); *A61P 35/00* (2018.01); *C07K 14/4748* (2013.01); *C07K 14/7051* (2013.01); *G01N 33/57496* (2013.01); *A61K 38/00* (2013.01); *A61K 2039/5158* (2013.01); *C07K 2319/00* (2013.01); *G01N 2333/47* (2013.01)

(58) Field of Classification Search
None
See application file for complete search history.

(56) References Cited

U.S. PATENT DOCUMENTS

| | | |
|---|---|---|
| 2001/0034042 A1 | 10/2001 | Srivastava |
| 2011/0059041 A1 | 3/2011 | Truneh et al. |
| 2014/0107039 A1 | 4/2014 | Allis et al. |
| 2017/0281742 A1 | 10/2017 | Okada et al. |

FOREIGN PATENT DOCUMENTS

| | | | |
|---|---|---|---|
| WO | 2013075237 A1 | 5/2013 | |
| WO | WO-2013075237 A1 * | 5/2013 | ............. A61P 35/00 |

OTHER PUBLICATIONS

"Prevent", available online at https://www.merriam-webster.com/dictionary/prevent, 13 pages (accessed on Jul. 2, 2022) (Year: 2022).*
Lowe et al., Cancers 11:24 pages (2019) (Year: 2019).*
"Histone H3 mutations in cancer," Abeam, available online at https://www.abcam.com/epigenetics/histone-h3-mutations-in-cancer, 9 pages (accessed on Jul. 2, 2022) (Year: 2022).*
Stetler et al., Prog. Neurobiol. 92:184-211 (2010) (Year: 2010).*
Kovalic, D. K. et al., "Wheat recombinant protein SEQ ID No. 152042." Database Geneseq [online], Feb. 3, 2011, XP002751291, retrieved from EBI accession No. GSP: A0109238.
La Rosa, T. J. et al., "Maize transcription factor protein sequence, 7139." Database Geneseq [online], Aug. 7, 2008, XP002751290, retrieved from EBI accession No. GSP:ARK49982.
Mitreva, M. et al., "The draft genome of the parasitic nematode Trichinella spiralis.—SubName: Full=Histone H3.2 {ECO:0000313\EMBL:EFV47787.1}; Flags: Fragment." Database UniProt [Online], Mar. 8, 2011, XP002751292, retrieved from EBI accession No. UNIPROT: E5T595.
Venneti, S. et al., "A sensitive and specific histopathologic prognostic marker for H3F3A K27M mutant pediatric glioblastomas." Acta Neuropathol, Sep. 2014, 128(5): 743-753.
BLAST comparison between instant SEQ ID No. 2 and NCBI Database AOi09238, 2 pages (accessed on Dec. 13, 2018) (Year: 2018).
Marcion et al., Cell Stress and Chaperones 20:61-72 (2015) (Year: 2015).

(Continued)

*Primary Examiner* — Thea D'Ambrosio
(74) *Attorney, Agent, or Firm* — SALIWANCHIK, LLOYD & EISENSCHENK

(57) ABSTRACT

The present invention pertains to novel immunogenic peptide sequences that can be used as vaccines in the treatment of cancer diseases such as brain cancers and specifically glioma. The cancer vaccines of the invention are designed based on the K27M mutated variant of the human Histone 3. Provided are further fusion proteins comprising the sequences of the cancer vaccines, nucleic acids encoding such vaccines, such as RNA vaccines, and vectors and host cells comprising these sequences. Furthermore the invention pertains to T cells and T cell receptors binding the cancer vaccines of the invention, preferably when presented by the human Major Histocompatibility Complex (MHC). The peptide immunogens of the invention elicit a HLA restricted immune response and therefore are of use in the treatment of cancer diseases, in particular glioma. Further aspects of the invention pertain to pharmaceutical compositions as well as diagnostic methods based on the immunogenic capacity of the disclosed peptides.

5 Claims, 2 Drawing Sheets
Specification includes a Sequence Listing.

(56) References Cited

OTHER PUBLICATIONS

Shiel, W.C., "Peptide", available online at https://www.medicinenet.com/script/main/art.asp?articlekey=24643, 1 page (2018) (Year: 2018).
UniProt Database, Accession No. P84243, 24 pages (2007) (Year: 2007).

* cited by examiner

SEQUENCE LISTING

```
<160> NUMBER OF SEQ ID NOS: 13

<210> SEQ ID NO 1
<211> LENGTH: 66
<212> TYPE: PRT
<213> ORGANISM: Homo sapiens

<400> SEQUENCE: 1

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Ser Ala Pro Ser Thr
            20                  25                  30

Gly Gly Val Lys Lys Pro His Arg Tyr Arg Pro Gly Thr Val Ala Leu
        35                  40                  45

Arg Glu Ile Arg Arg Tyr Gln Lys Ser Thr Glu Leu Leu Ile Arg Lys
    50                  55                  60

Leu Pro
65

<210> SEQ ID NO 2
<211> LENGTH: 66
<212> TYPE: PRT
<213> ORGANISM: Homo sapiens

<400> SEQUENCE: 2

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Met Ser Ala Pro Ser Thr
            20                  25                  30

Gly Gly Val Lys Lys Pro His Arg Tyr Arg Pro Gly Thr Val Ala Leu
        35                  40                  45

Arg Glu Ile Arg Arg Tyr Gln Lys Ser Thr Glu Leu Leu Ile Arg Lys
    50                  55                  60

Leu Pro
65

<210> SEQ ID NO 3
<211> LENGTH: 10
<212> TYPE: PRT
<213> ORGANISM: Homo sapiens

<400> SEQUENCE: 3

Lys Gln Leu Ala Thr Lys Ala Ala Arg Met
1               5                   10

<210> SEQ ID NO 4
<211> LENGTH: 10
<212> TYPE: PRT
<213> ORGANISM: Homo sapiens
```

```
<400> SEQUENCE: 4

Gln Leu Ala Thr Lys Ala Ala Arg Met Ser
1               5                   10

<210> SEQ ID NO 5
<211> LENGTH: 10
<212> TYPE: PRT
<213> ORGANISM: Homo sapiens

<400> SEQUENCE: 5

Leu Ala Thr Lys Ala Ala Arg Met Ser Ala
1               5                   10

<210> SEQ ID NO 6
<211> LENGTH: 10
<212> TYPE: PRT
<213> ORGANISM: Homo sapiens

<400> SEQUENCE: 6

Ala Thr Lys Ala Ala Arg Met Ser Ala Pro
1               5                   10

<210> SEQ ID NO 7
<211> LENGTH: 10
<212> TYPE: PRT
<213> ORGANISM: Homo sapiens

<400> SEQUENCE: 7

Thr Lys Ala Ala Arg Met Ser Ala Pro Ser
1               5                   10

<210> SEQ ID NO 8
<211> LENGTH: 10
<212> TYPE: PRT
<213> ORGANISM: Homo sapiens

<400> SEQUENCE: 8

Lys Ala Ala Arg Met Ser Ala Pro Ser Thr
1               5                   10

<210> SEQ ID NO 9
<211> LENGTH: 10
<212> TYPE: PRT
<213> ORGANISM: Homo sapiens

<400> SEQUENCE: 9

Ala Ala Arg Met Ser Ala Pro Ser Thr Gly
1               5                   10

<210> SEQ ID NO 10
<211> LENGTH: 10
<212> TYPE: PRT
<213> ORGANISM: Homo sapiens

<400> SEQUENCE: 10

Ala Arg Met Ser Ala Pro Ser Thr Gly Gly
1               5                   10

<210> SEQ ID NO 11
<211> LENGTH: 10
<212> TYPE: PRT
<213> ORGANISM: Homo sapiens

<400> SEQUENCE: 11
```

```
Arg Met Ser Ala Pro Ser Thr Gly Gly Val
1               5                   10

<210> SEQ ID NO 12
<211> LENGTH: 10
<212> TYPE: PRT
<213> ORGANISM: Homo sapiens

<400> SEQUENCE: 12

Met Ser Ala Pro Ser Thr Gly Gly Val Lys
1               5                   10

<210> SEQ ID NO 13
<211> LENGTH: 27
<212> TYPE: PRT
<213> ORGANISM: Homo sapiens

<400> SEQUENCE: 13

Lys Ala Pro Arg Lys Gln Leu Ala Thr Lys Ala Ala Arg Met Ser Ala
1               5                   10                  15

Pro Ser Thr Gly Gly Val Lys Lys Pro His Arg
            20                  25
```

HISTONE ANTI-CANCER VACCINES

CROSS REFERENCE TO A RELATED APPLICATION

This application is a Continuation Application of Ser. No. 15/735,046, filed Dec. 8, 2017; which is a National Stage Application of International Application Number PCT/EP2016/066563, filed Jul. 12, 2016; which claims priority to European Patent Application No. 15176879.3, filed Jul. 15, 2015, both of which are incorporated herein by reference in their entirety.

The Sequence Listing for this application is labeled "SeqList-06Dec17-ST25.txt", which was created on Dec. 6, 2017, and is 4 KB. The entire content is incorporated herein by reference in its entirety.

FIELD OF THE INVENTION

The present invention pertains to novel immunogenic peptide sequences that can be used as vaccines in the treatment of cancer diseases such as brain cancers and specifically glioma.

The cancer vaccines of the invention are designed based on the K27M mutated variant of the human Histone 3. Provided are further fusion proteins comprising the sequences of the cancer vaccines, nucleic acids encoding such vaccines, such as RNA vaccines, and vectors and host cells comprising these sequences. Furthermore the invention pertains to T cells and T cell receptors binding the cancer vaccines of the invention, preferably when presented by the human Major Histocompatibility Complex (MHC). The peptide immunogens of the invention elicit a HLA restricted immune response and therefore are of use in the treatment of cancer diseases, in particular glioma. Further aspects of the invention pertain to pharmaceutical compositions as well as diagnostic methods based on the immunogenic capacity of the disclosed peptides.

BACKGROUND OF THE INVENTION

Primary brain tumors consist of a diverse group of neoplasms, derived from various different cell lineages. Pursuant to a World Health Organization categorization, tumors of the central nervous system are classified as astrocytic, oligodendroglial, or mixed (oligoastrocytic). These tumors are further classified by subtypes and are graded, based on histology, from I to IV, with grade IV being the most aggressive. Every year, 18,500 new brain tumors are diagnosed in the United States. Of these tumors, 50% are gliomas; 50% of these gliomas are glioblastoma multiforme (GBM), with the dismal survival prognosis of 10-12 months.

Gliomas are heterogeneous in their cellular content and can be divided into groups of astrocytomas, anablastic astrocytomas and glioblastoma multiformes. Traditional approaches to therapeutic intervention have relied upon surgery, chemotherapy, or radiotherapy. Recent advances in molecular genetics have revealed many genetic mutations and associated signaling pathways that may play a causative role in the generation of gliomas. While these advances have provided numerous candidate pathways that can be utilized in the development of rational therapy rooted in the biology of the disease, it remains to be seen whether such approaches will come to fruition. As such, there is a continued need for gliomal therapies. Paediatric glioblastomas (GBM) are highly aggressive and lethal tumors. Recent sequencing studies have shown that ~30% of paediatric GBM and ~80% of diffuse intrinsic pontine gliomas show K27M mutations in the H3F3A gene, a variant encoding histone H3.3. H3F3A K27M mutations lead to global reduction in H3K27me3 and the mutation is used as prognostic marker indicating a poor prognosis (Venneti S, et al. Acta Neuropathol, 2014 Nov. PMID 25200322).

T cell-mediated anti-tumor immunity plays a role in regulating tumor growth, placing selective pressure on the antigenically-heterogeneous cancer cell population throughout disease progression. Most tumor-associated antigens (TAAs) recognized by T cells are "self" antigens that may be quantitatively over-expressed by tumor cells or are selectively mutated in tumor cells (mutated TAA) of one or more histologic types. Clinical trials implementing vaccines and immunotherapies targeting such antigens have exhibited success in promoting increased numbers of specific CD4+ and/or CD8+ T cell populations in the peripheral blood of patients. There is a need to identify additional tumor associated antigens or combinations of antigens that can be used for cancer immunotherapy.

Therefore there is a continuing need to provide novel tumor associated antigens, as peptide or nucleic acids, which can be used as anti-cancer vaccines for the treatment of proliferative diseases. In particular the present invention seeks to provide new therapeutics and companion diagnostics for patients suffering from K27M Histone H3.3 associated glioma.

DETAILED DESCRIPTION

The above problem is solved in a first aspect by a peptide comprising an amino acid sequence corresponding to the K27M variant of human Histone H3.3, wherein the peptide is not the full length K27M variant of human Histone 113.3. The sequence of the first (N-terminal) 1 to 66 amino acid positions of the wild-type Histone H3.3 (SEQ ID NO 1) and the K27M variant (SEQ ID NO 2) are provided herein below. The full length sequences of both Histone H3.3 versions are known to the skilled person. Preferred is a peptide, comprising an amino acid sequence corresponding to the K27M variant of human Histone H3.3, wherein the peptide comprises the K27M mutated amino acid position and is not the full length K27M variant of human Histone H3.3.

A K27M variant of human Histone H3.3 in context of the present invention shall refer to a human Histone H3.3 protein having a lysine to methionine amino acid substitution at position 27 (K27M).

Preferably the peptide of the invention is an immunogenic peptide. In the context of the present invention, the term "immunogenic peptide" is intended to mean a peptide capable of inducing a specific cytotoxic T-lymphocyte (CTL) response against the K27M variant of human Histone H3.3. The peptide of the invention may have the capacity of binding to the Major Histocompatibility Complex (MHC), preferably MHC Class I. Therefore, a preferred peptide of the invention is capable of eliciting a T-cell mediated immune response, preferably a CD8 positive T-cell mediated immune response.

The term "T cell mediated immune response" means an immune response in which T cells directly or indirectly mediate or otherwise contribute to an immune response in a mammal. The T cell mediated immune response may be associated with cell mediated effects, cytokine mediated effects, etc., and even effects associated with B cells if the B cells are stimulated, for example, by the cytokines secreted by T cells.

In preferred embodiments of the invention the immunogenic peptide of the invention elicits an immune response which is specific for the K27M variant of human Histone H3.3. "Specific" in this context shall preferably exclude peptide which elicit a stronger or any immune response at all against the wild-type version of human Histone H3.3.

In some embodiments the peptide according to the invention may have a variable length, however, with the proviso that the peptide shall not comprise the full-length sequence of K27M variant of human Histone H3.3. Preferably the peptide has a length of at least 100 amino acids, preferably of at least 50, 40, 30, 25, 20, 19, 18, 17, 16, 15, 14, 13, 12, 10, more preferably of at least 9 or 8 amino acids. Preferred embodiments of the invention pertain to peptides consisting of a sequence of 8 amino acids. Other preferred embodiments of the invention pertain to peptides consisting of a sequence of 9 amino acids. Most preferred embodiments of the invention pertain to peptides consisting of a sequence of 10 amino acids. Other preferred embodiments of the invention pertain to peptides consisting of a sequence of 11 amino acids.

The sequence of the peptide of the invention may preferably comprise the K27M mutation of human Histone H3.3. Therefore, the sequence of the peptide of the invention shall overlap with or span the K27M sequence position as indicated in SEQ ID NO 2 below.

In one preferred embodiment of the invention the peptide comprises, consists essentially of, or consists of, (i) an amino acid sequence selected from any of SEQ ID NO: 3 to 13, or (ii) an amino acid sequence having a sequence identity of at least 80%, preferably 85%, 90%, 95%, 98%, or 99% compared to a sequence selected from any of SEQ ID NO: 3 to 13. Most preferred for all aspects and embodiments of the invention is the peptide of SEQ ID NO 3, 11, or 13 most preferred of SEQ ID NO 11, which according to the examples displayed a surprisingly strong immune response in a HLA-A*02 restricted manner.

The peptide of the invention may preferably be a synthetic peptide, a peptide variant, a mutant peptide, a chemically modified peptide, a retro-inverse peptide, or a peptide comprising at least one non-peptide bond. Such peptide variants are known in the art.

Importantly it is noted that the peptide sequences of the invention all comprise the K27M mutation and hence do not constitute products of nature but are mutated versions of the naturally occurring epitope of human Histone H3.3. However, in another preferred embodiment the peptide of the invention is synthetic and in the form of a salt or pharmaceutically acceptable salt.

As already mentioned above, the immunogenic peptide of the invention has the ability of eliciting an immune response. Therefore, as other immunogenic epitopes, the peptide of the invention is presented by an antigen presenting cell, such as a dendritic cell or tumor cell, via the MHC and then, when bound to the MHC, the peptide is capable of binding to a T-cell receptor (TCR)—thereby getting recognized by the TCR. The TCR is expressed on the surface of T cells and when recognizing a MHC bound peptide initiates immune signalling which finally yields into a full immune response. Preferably the peptide elicits an HLA class I restricted immune response in a mammal. For example it is preferred that the peptide is capable of binding the HLA class I complex, preferably wherein the peptide is specific for HLA class I haplotype A*2.

The invention includes derivatives of the peptides or proteins described herein which are comprised by the terms "peptide" and "protein". According to the invention, "derivatives" of proteins and peptides are modified forms of proteins and peptides. Such modifications include any chemical modification and comprise single or multiple substitutions, deletions and/or additions of any molecules associated with the protein or peptide, such as carbohydrates, lipids and/or proteins or peptides. In one embodiment, "derivatives" of proteins or peptides include those modified analogs resulting from glycosylation, acetylation, phosphorylation, amidation, palmitoylation, myristoylation, isoprenylation, lipidation, alkylation, derivatization, introduction of protective/blocking groups, proteolytic cleavage or binding to an antibody or to another cellular ligand. The term "derivative" also extends to all functional chemical equivalents of said proteins and peptides. Preferably, a modified peptide has increased stability and/or increased immunogenicity.

Also included are mimetics of peptides. Such mimetics may comprise amino acids linked to one or more amino acid mimetics (i.e., one or more amino acids within the peptide may be replaced by an amino acid mimetic) or may be entirely non-peptide mimetics. An amino acid mimetic is a compound that is conformational similar to an amino acid, e.g. such that it can be substituted for an amino acid without substantially diminishing the ability to react with T cell lines or clones. A non-peptide mimetic is a compound that does not contain amino acids, and that has an overall conformation that is similar to a peptide, e.g. such that the ability of the mimetic to react with T cell lines or clones is not substantially diminished relative to the ability of a given peptide.

According to the invention, a variant, derivative, modified form, fragment, part or portion of an amino acid sequence, peptide or protein preferably has a functional property of the amino acid sequence, peptide or protein, respectively, from which it has been derived, i.e. it is functionally equivalent. In one embodiment, a variant, derivative, modified form, fragment, part or portion of an amino acid sequence, peptide or protein is immunologically equivalent to the amino acid sequence, peptide or protein, respectively, from which it has been derived. In one embodiment, the functional property is an immunological property. A particular property is the ability to form a complex with MHC molecules and, where appropriate, generate an immune response, preferably by stimulating cytotoxic or T helper cells.

In a further aspect, the invention relates to a cell that presents the peptide of the invention or a procession product thereof, wherein the procession product preferably is a peptide having the given amino acid sequence, i.e. an amino acid sequence selected from the group consisting of SEQ ID NO 2 to 13, or a variant of said amino acid sequence. The cell may present the peptide or a procession product thereof by MHC molecules on its surface. In one embodiment, the cell endogenously expresses an MHC molecule. In a further embodiment, the cell recombinantly expresses an MHC molecule. In one embodiment, the MHC molecules of the cell are loaded (pulsed) with the peptide by addition of the peptide to the cell. The cell may recombinantly express the peptide and present said peptide or a procession product thereof on the cell surface. The cell is preferably non-proliferative. In a preferred embodiment, the cell is an antigen-presenting cell such as a dendritic cell, a monocyte or a macrophage.

Another aspect of the invention then pertains to a fusion protein comprising an amino acid sequence composed of
i. the amino acid sequences of at least two, preferably three or more, different peptides according to the invention, or ii. the amino acid sequence of a peptide according to the invention, and the amino acid sequence of a heat shock protein (HSP) binding domain, or iii. the amino acid sequence of a peptide according to the invention, and the amino acid sequence of a HSP or a functional variant thereof.

Fusion proteins of the invention may alternatively comprise a peptide of the invention and one or more further N- and/or C-terminal non-K27M amino acid sequences. Such N- and/or C-terminal non-K27M amino acid sequences do not correspond to the N- or, respectively, C-terminal, amino acid sequences directly next of the respective peptide-sequence stretch in the K27M-sequence.

Yet another aspect of the invention pertains to a nucleic acid comprising a nucleotide sequence encoding for a peptide of the invention, or encoding for a fusion of the invention, wherein the nucleic acid does not encode the full length K27M variant of human Histone H3.3. A nucleic acid according to the invention is preferably a DNA, RNA, PNA, or LNA, and may be single stranded or double stranded.

Preferred embodiments of the invention pertain to single or double stranded RNA, preferably an mRNA, which can be used as an RNA vaccine.

A vaccine is typically understood to be a prophylactic or therapeutic material providing at least one antigen, preferably an immunogen such as the herein described peptide immunogens or RNA immunogens. For example, the vaccine may comprise a nucleic acid, such as an RNA (e.g. RNA vaccine), which codes for a peptide or protein that comprises the antigen as described herein. The antigen or immunogen stimulates the body's adaptive immune system to provide an adaptive immune response. Furthermore, in the context of the present aspect of nucleic acids, the vaccine is preferably an RNA vaccine. An RNA vaccine is defined herein as a vaccine comprising at least one RNA molecule comprising at least one open reading frame (ORF) coding for at least one antigen, preferably the antigen being a protein comprising or consisting of an amino acid sequence as shown in SEQ ID NO: 2 to 13. In the context of the present invention, the at least one RNA molecule comprised by the vaccine is preferably an isolated RNA molecule. This at least one RNA is preferably viral RNA, self-replicating RNA (replicon) or most preferably mRNA. Also included herein are RNA/DNA hybrids which means that the at least one RNA molecule of the RNA vaccine consists partially of ribonucleotides and partially of deoxyribonucleotides. In this context, the at least one RNA of the RNA vaccine consists to at least 50% of ribonucleotides, more preferably to at least 60%, 70%, 80%, 90% and most preferably to 100%. In this context, the at least one RNA of the RNA vaccine can also be provided as complexed RNA or mRNA, as virus particle and as replicon particle as defined herein.

Another aspect of the invention then pertains to an expression vector comprising a nucleic acid of the invention.

The term "vector" as used herein includes any vectors known to the skilled person including plasmid vectors, cosmid vectors, phage vectors such as lambda phage, viral vectors such as adenoviral or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems.

Cloning vectors are generally used to engineer and amplify a certain desired DNA fragment and may lack functional sequences needed for expression of the desired DNA fragments.

The above problem of the invention is also solved by an in-vitro method for producing a peptide immunogen of the invention; the method comprises the recombinant expression of the peptide in a host cell, and isolating the peptide from the host cell or its culture medium. In this aspect the host cell may preferably comprise a nucleic acid according or an expression vector as described herein before. However, the peptides of the invention may also be obtained by any other method known to the skilled person, for example, by recombinantly expressing the full length K27M variant and subsequent fragmentation.

Some therapeutic methods are based on a reaction of the immune system of a patient, which results in a lysis of diseased cells which present an antigen with class I MHC. In this connection, for example autologous cytotoxic T lymphocytes specific for a complex of an immunogenic peptide and an MHC molecule may be administered to a patient having a disease, such as a brain cancer. The production of such cytotoxic T lymphocytes in vitro is known. Generally, a sample containing cells such as blood cells is taken from the patient and the cells are contacted with a cell which presents the complex and which can cause propagation of cytotoxic T lymphocytes (e.g. dendritic cells). The target cell may be a transfected cell such as a COS cell. These transfected cells present the desired complex on their surface and, when contacted with cytotoxic T lymphocytes, stimulate propagation of the latter. The clonally expanded autologous cytotoxic T lymphocytes are then administered to the patient.

Furthermore, cells presenting the desired complex (e.g. dendritic cells) may be combined with cytotoxic T lymphocytes of healthy individuals or another species (e.g. mouse) which may result in propagation of specific cytotoxic T lymphocytes with high affinity. The high affinity T cell receptor of these propagated specific T lymphocytes may be cloned and optionally humanized to a different extent, and the T cell receptors thus obtained then transduced via gene transfer, for example using retroviral vectors, into T cells of patients. Adoptive transfer may then be carried out using these genetically altered T lymphocytes (Stanislawski et al. (2001), Nat. Immunol. 2:962-70; Kessels et al. (2001), Nat. Immunol. 2:957-61.

In one embodiment the invention pertains to an in-vitro method for producing an activated T-lymphocyte, comprising the step of contacting a T-cell in-vitro with an MHC class I or II molecule binding to, and presenting, an immunogenic peptide of the invention, wherein the MHC class I or II molecule binding to, and presenting, the peptide, is expressed on a suitable antigen presenting cell, or is in the form of a suitable antigen presenting construct. The contacting is preferably performed for an amount of time sufficient for the T-cell to become activated.

The T-cell may be a CD8 positive T-cell and the MHC molecule is accordingly an MHC class I molecule, or, the T-cell is a CD4 positive T-cell and the MHC molecule is an MHC class II molecule. Most preferably the T cell is a human T cell.

After activating the T-cell the method may comprise the further step of in-vitro propagating the activated T-lymphocyte. Propagation means in this context an in-vitro expansion of the activated T cells in order to obtain sufficient amounts for therapeutic purposes.

The invention also pertains to an isolated T-lymphocyte, preferably a CD4 or CD8 positive T-cell, which is obtainable by the above described method for producing an activated T-lymphocyte.

The term "cell" or "host cell" preferably is an intact cell, i.e. a cell with an intact membrane that has not released its normal intracellular components such as enzymes, organelles, or genetic material. An intact cell preferably is a viable cell, i.e. a living cell capable of carrying out its normal metabolic functions. Preferably said term relates according to the invention to any cell which can be transformed or transfected with an exogenous nucleic acid. The term "cell" includes according to the invention prokaryotic cells (e.g., $E.$ $coli$) or eukaryotic cells (e.g., dendritic cells, B cells, CHO cells, COS cells, K562 cells, HEK293 cells, HELA cells, yeast cells, and insect cells). The exogenous nucleic acid may be found inside the cell (i) freely dispersed as such, (ii) incorporated in a recombinant vector, or (iii) integrated into the host cell genome or mitochondrial DNA. Mammalian cells are particularly preferred, such as cells from humans, mice, hamsters, pigs, goats, and primates. The cells may be derived from a large number of tissue types and include primary cells and cell lines. Specific examples include keratinocytes, peripheral blood leukocytes, bone marrow stem cells, and embryonic stem cells. In further embodiments, the cell is an antigen-presenting cell, in particular a dendritic cell, a monocyte, or macrophage.

Another aspect then pertains to an isolated T-lymphocyte which elicits a T-cell response via its T-cell receptor in response to a peptide of the invention, preferably wherein the T-cell is a CD8 or CD4 positive T-cell, most preferably a CD8 positive T-cell.

Yet another aspect pertains to an in-vitro method for producing a T-cell receptor (TCR), the method comprising isolating a T-cell receptor from an activated T-lymphocyte of the invention Alternatively, the method for producing a TCR of the invention comprises the steps of, immunizing a non-human animal, preferably a mouse or rat, with a peptide of the invention, a fusion protein of the invention, a nucleic acid of the invention, or an expression vector of the invention, and thereby inducing an adaptive immune response in said non-human animal isolating from the immunized non-human animal T-cells which are reactive to the peptide of the invention, and isolating from said T-cells the T-cell receptor.

Furthermore provided is an isolated T-cell receptor which is obtainable by a method according to the present disclosure.

Also provided is an isolated T-cell receptor, wherein the TCR is characterized in that it comprises a variable domain with a specific binding affinity to a peptide of the invention. Preferably the binding affinity is mediated by the variable domain, and therein by the Complementary Determining Regions (CDR). The TCR can bind the peptide preferably when it is bound/presented by MHC.

Another aspect provides a host cell comprising a peptide, a fusion protein, a nucleic acid or an expression vector of the invention.

Also a pharmaceutical composition comprising the various compounds and compositions of the invention is provided. The pharmaceutical composition of the invention may optionally comprise pharmaceutically acceptable excipients and/or carriers. The pharmaceutical composition of the invention may be in the form of a vaccine composition, or in the form of a composition suitable for cell based therapy.

The pharmaceutical compositions of the invention are preferably sterile and contain an effective amount of the therapeutically active substance to generate the desired reaction or the desired effect.

Pharmaceutical composition of the invention may comprise a pharmaceutically compatible carrier. The term "carrier" refers to an organic or inorganic component, of a natural or synthetic nature, in which the active component is combined in order to facilitate application. According to the invention, the term "pharmaceutically compatible carrier" includes one or more compatible solid or liquid fillers, diluents or encapsulating substances, which are suitable for administration to a patient. The components of the pharmaceutical composition of the invention are usually such that no interaction occurs which substantially impairs the desired pharmaceutical efficacy.

The pharmaceutical compositions of the invention may contain suitable buffer substances such as acetic acid in a salt, citric acid in a salt, boric acid in a salt and phosphoric acid in a salt.

The pharmaceutical compositions may, where appropriate, also contain suitable preservatives such as benzalkonium chloride, chlorobutanol, paraben and thimerosal.

The pharmaceutical compositions are usually provided in a uniform dosage form and may be prepared in a manner known per se. Pharmaceutical compositions of the invention may be in the form of capsules, tablets, lozenges, solutions, suspensions, syrups, elixirs or in the form of an emulsion, for example.

Compositions suitable for parenteral administration usually comprise a sterile aqueous or non-aqueous preparation of the active compound, which is preferably isotonic to the blood of the recipient. Examples of compatible carriers and solvents are Ringer solution and isotonic sodium chloride solution. In addition, usually sterile, fixed oils are used as solution or suspension medium.

The various compounds and compositions of the present invention are preferably for use in the treatment of a disease. The disease is in some embodiments a proliferative disease, such as a cancer disease. The cancer may be characterized by the expression of the K27M mutated variant of human Histone H3.3. A preferred cancer suitable to be treated in accordance with the invention is a cancer of the central nervous system, preferably a glioma, such as an astrocytoma. Preferred brain cancers are paediatric astrocytoma characterized by the expression of the K27M mutant human Histone H3.3.

Hence, the invention also pertains to a method of treating a cancer in a patient, the method comprising the administration of an effective amount of any of the aforementioned products or compositions to the patient.

The agents described herein are administered in effective amounts. An "effective amount" refers to the amount which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition.

An effective amount of an agent described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the agents described herein may depend on several of such parameters. In the case that a reaction in a patient is insufficient with an initial dose, higher doses (or effectively higher doses achieved by a different, more localized route of administration) may be used.

Then another aspect of the invention relates to an in-vitro method for diagnosing cancer in a subject, the method comprising
i. Providing a biological sample of the subject and suspected to contain antibodies,
ii. in-vitro detecting in the biological sample the presence or absence of an antibody which is specific for the Histone H3.3 K27M variant and not specific for the wild-type variant of human Histone H3.3, wherein the presence or absence of the antibody is detected using a peptide library composed of at least one K27M-peptide, wherein the at least one K27M peptide comprises a sequence of at least 8 contiguous (adjoining) amino acids of the amino acid sequence of the K27M variant of human Histone H3.3, said at least 8 adjacent amino acids comprising the K27M mutation of human Histone H3.3,
wherein the presence of an antibody which is specific for the Histone H3.3 K27M variant in the biological sample is indicative for the presence of a cancer expressing the K27M variant of human Histone H3.3 in the subject.

The method is based on the idea that if a K27M expressing cancer is present in a subject to be diagnosed, this subject will produce antibodies directed against this mutated cancer antigen. On the other hand, a healthy subject will not have antibodies specific for the Histone H3.3 K27M variant. Thus, by testing the absence or presence of an antibody specific for the K27M mutation in a subject the cancer disease can be diagnosed. The presence of an antibody specifically binding the at least one K27M peptide in the peptide library thus indicates the presence of an antibody which is specific for the Histone H3.3 K27M variant in the biological sample and thereby indicates the presence of the cancer.

Antibody-binding is preferably tested immunological. For example after contacting the peptide library with the biological sample, unbound or unspecifically bound antibodies can be removed—for example by one or more washing steps. Thereafter only such antibodies remain which have a specific K27M binding and thus are bound to the K27M peptide within the peptide library. Using a secondary anti-human antibody coupled to a label allows generating a detectable signal depending on the absence or presence of any bound antibody.

The term "K27M peptide" in context of the present invention shall refer to an immunogenic peptide as described herein above. Such a peptide is preferably a 8mer to 40mer, and comprises a sequence spanning the K27M mutation of SEQ ID NO 2. Preferred K27M peptide libraries are composed of 8mers, 9mers, 10mers or 11mers.

In one preferred embodiment of this aspect the at least one K27M peptide has a length of 100 to 8, preferably 50 to 8, more preferably 40 to 8, 30 to 8, or 20 to 8 amino acids. Alternatively or additionally the at least 8 contiguous amino acids of the amino acid sequence of the K27M variant of human Histone H3.3 are derived from amino acid position 1 to 66 of the K27M variant of human Histone H3.3, or from SEQ ID NO 2.

In another embodiment the peptide library is composed of a plurality of non-identical K27M-peptides, the plurality of non-identical K27M-peptides being at least 2, 3, 4, 5, 6, 7, 8, 9, 10, 15, 20, 30, 50, 100 or more K27M-peptides. A plurality of non-identical K27M peptides shall be a collection of peptides each having a different sequence but still comprising the K27M mutation. The peptide library therefore constitutes a collection of possible histone K27M epitopes. Preferably in some embodiments the library further comprises as a control at least one peptide, preferably more, which in its sequence does not comprising the K27M mutation. Furthermore, the peptide library may comprise as a positive control an immunogenic peptide as described herein above, preferably a peptide having of SEQ ID NO: 3 to 13.

In an additional embodiment the peptide library is composed of all possible (theoretical) non-identical K27M peptides having a sequence comprising 8 to 40 contiguous amino acids of the amino acid sequence of position 1 to 66 of the K27M variant of human Histone H3.3.

In this context the subject is preferably a human, preferably a non-adult human patient. In context of the present invention the term "biological sample" refers to a blood sample, preferably a serum sample. However any sample which could contain antibodies against the K27M variant of human Histone H3.3 could be used as a biological sample.

The cancer to be diagnosed is preferably a brain cancer such as a glioma, preferably an astrocytoma, more preferably a paediatric astrocytoma.

The herein described method of the invention may further comprise the step of quantifying the amount of antibody in the biological sample binding to the at least one K27M-peptide.

The herein disclosed diagnostic method is preferably based on an ELISA assay, such as a Sandwich-ELISA. Alternatively, the K27M peptides of the peptide library may be directly coupled on to a solid support. For example the K27M peptides may be spotted to a glass slide. Any other state of the art peptide array technology may be employed for the peptide library of the invention.

Furthermore provided is a diagnostic kit for performing the in-vitro method for diagnosing cancer in a subject described herein before, the kit comprising a K27M peptide library composed of at least one K27M-peptide, wherein the at least one K27M peptide comprises a sequence of at least 8 contiguous (adjoining) amino acids of the amino acid sequence of the K27M variant of human Histone H3.3, said at least 8 adjacent amino acids comprising the K27M mutation of human Histone H3.3.

Preferably the K27M peptides of the peptide library of the invention are provided bound to a solid support such as a glass slide or peptide chip.

The diagnostic kit of the invention may further include components necessary for conducting an ELISA assay with the peptide library.

The present invention also provides an in-vitro method for monitoring a cancer disease in a subject, the method comprising performing the diagnostic method described above, wherein an increase of detected antibody over time indicates a worsening of the cancer disease in the subject, whereas a decrease of the amount of detected antibody over time indicates an alleviation of the disease.

The present invention will now be further described in the following examples with reference to the accompanying figures and sequences, nevertheless, without being limited thereto. For the purposes of the present invention, all references as cited herein are incorporated by reference in their entireties. In the Figures and sequences:

BRIEF DESCRIPTION OF THE SEQUENCES (amino acid 1 to 66 of wild-type human Histone H3.3.)
SEQ ID NO 1
ARTKQTARKSTGGKAPRKQLATKAAR<u>K</u>SAPSTGGVKKPHRYRPGTVALRE
IRRYQKSTELLIRKLP (amino acid 1 to 66 of the K27M variant of human Histone H3.3.)
SEQ ID NO 2
ARTKQTARKSTGGKAPRKQLATKAAR<u>M</u>SAPSTGGVKKPHRYRPGTVALRE
IRRYQKSTELLIRKLP (peptide corresponding to amino acids 18-27 of K27M Histone H3.3)
SEQ ID NO 3
KQLATKAAR<u>M</u>

(peptide corresponding to amino acids 19-28 of K27M Histone H3.3)
SEQ ID NO 4
QLATKAAR<u>M</u>S (peptide corresponding to amino acids 20-29 of K27M Histone H3.3)
SEQ ID NO 5
LATKAAR<u>M</u>SA (peptide corresponding to amino acids 21-30 of K27M Histone H3.3)
SEQ ID NO 6
ATKAAR<u>M</u>SAP (peptide corresponding to amino acids 22-31 of K27M Histone H3.3)
SEQ ID NO 7
TKAAR<u>M</u>SAPS (peptide corresponding to amino acids 23-32 of K27M Histone H3.3)
SEQ ID NO 8
KAAR<u>M</u>SAPST (peptide corresponding to amino acids 24-33 of K27M Histone H3.3)
SEQ ID NO 9
AAR<u>M</u>SAPSTG (peptide corresponding to amino acids 25-34 of K27M Histone H3.3)
SEQ ID NO 10
AR<u>M</u>SAPSTGG (peptide corresponding to amino acids 26-35 of K27M Histone H3.3)
SEQ ID NO 11
R<u>M</u>SAPSTGGV (peptide corresponding to amino acids 27-36 of K27M Histone H3.3)
SEQ ID NO 12
<u>M</u>SAPSTGGVK (peptide corresponding to amino acids 14-40 of K27M Histone H3.3)
SEQ ID NO 13
KAPRKQLATKAAR<u>M</u>SAPSTGGVKKPHR

Examples

For malignant brain tumors, progress in molecular diagnostics including genome-wide sequencing led to identification of distinct subgroup-defining genetic alterations. As these driver mutations may result in tumor-specific neoantigens they represent promising immunotherapeutic targets. One mutation frequently occurring in pediatric brain stem and adult gliomas is a point mutation in the histon-3 gene (H3F3A) leading to an amino acid exchange from lysine to arginine at position 27 (K27M).

Figure 1:
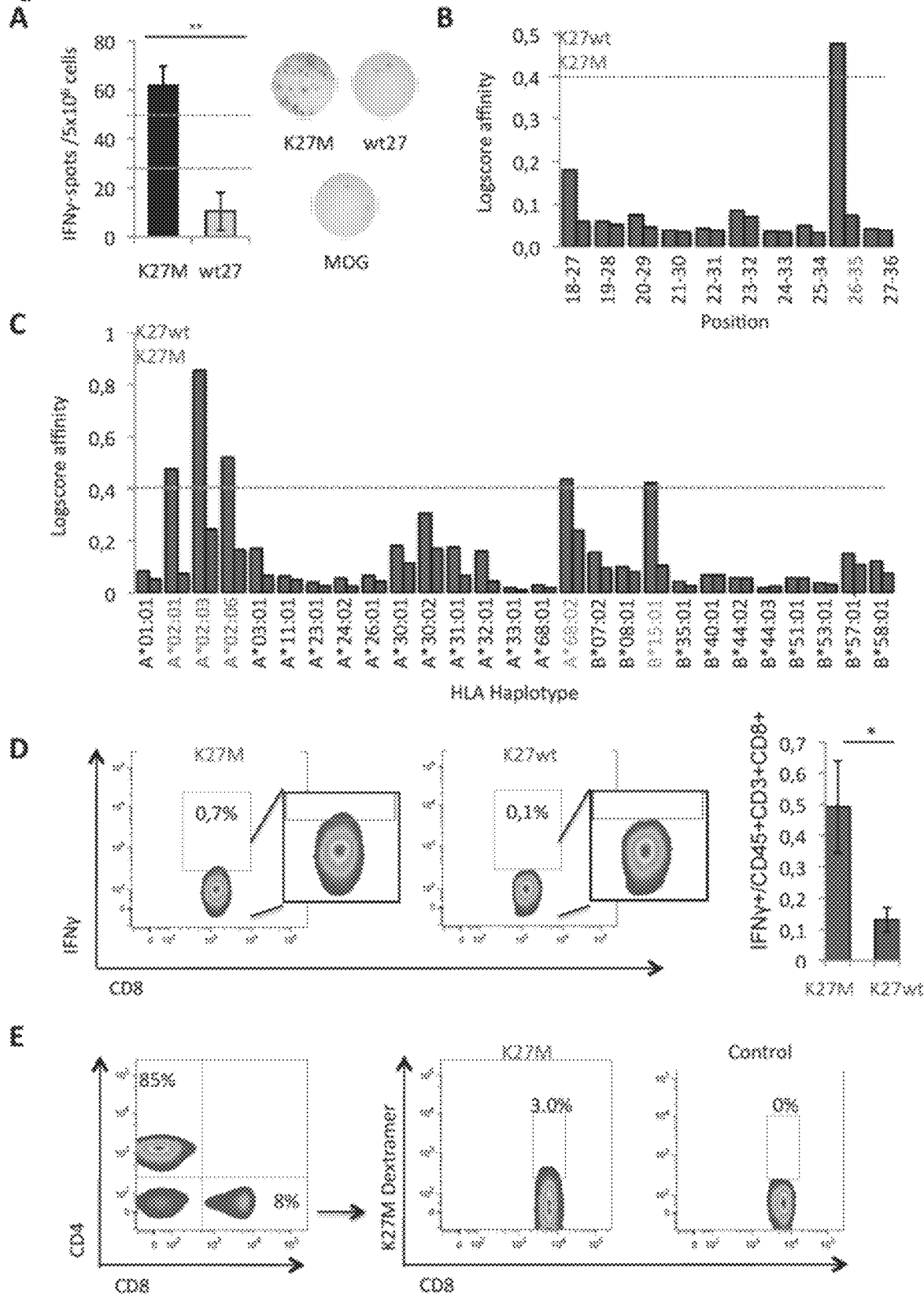
FIG. 1: (A) H3.3 K27M peptide vaccination induces mutation-specific IFNγ immune responses in MHC-humanized mice: ELISpots of IFNγ splenocyte responses to H3.3 K27M$_{14-40}$ (black) or K27wt$_{14-40}$ (grey) after vaccination of A2.DR1 mice with H3.3 K27M$_{14-40}$ or vehicle control in Montanide®. Numbers of spots to MOG$_{35-55}$ as negative control were subtracted. Mean+/−s.e.m. of n=4 mice per group and representative ELISpots are shown. **p<0.01. (B/C): H3.3-peptide libraries are used to assess MHC binding epitopes in silico: MHC peptide binding predictions for H3.3 K27M (red)- and K27 wt (blue)-containing 10-mer peptides to HLA-A*02:01 using NetMHC algorithm (B) and MHC peptide binding analysis for H3.3 K27M$_{26-35}$ (red) or K27 wt$_{26-35}$ (blue) depending on MHC-class-I haplotype (C). Peptides with logscore affinity >0.4 are defined as potential binders. (D) H3.3 K27M$_{26-35}$ peptide vaccination induces a mutation-specific CD8-driven T-cell response in MHC-humanized mice: Representative intracellular flow cytometry of splenocyte IFNγ-responses to H3.3 K27M$_{26-35}$ or K27 wt$_{26-35}$ after vaccination of three A2.DR1 mice with H3.3 K27M$_{26-35}$ in Montanide®. Re-stimulation with the vehicle DMSO served as control; gated on CD45+ CD3+ CD8+ cells. (E) H3.3 K27M$_{26-35}$-specific CD8-positive T-cells are detected with HLA-A2 multimers: Representative flow cytometry of splenocyte CD4/CD8 T-cell ratio and CD8 T-cell responses to H3.3 K27M$_{26-35}$-specific dextramers or control after vaccination of three A2.DR1 mice with H3.3 K27M$_{26-35}$ in Montanide®; gated on CD45+ CD3+ cells.

Vaccination of MHC-humanized HLA-A*0201 HLA-DRA*0101 HLA-DRB*0101 transgenic mice (A2.DR1 mice) with a 27-mer peptide containing the H3.3 K27M mutation at position 14 (K27M$_{14-40}$) resulted in a robust and mutation-specific IFNγ T cell response (FIG. 1 A). Assuming a MHC class I driven CD8-positive T cell response MHC binding prediction algorithms were used to further localize the relevant MHC class I epitope: in silico analyses with a peptide library containing the mutated and wild type sequences suggested a 10-mer harboring the point mutation at position 2 (K27M$_{26-35}$) as potential binder. Importantly, the corresponding wild type sequence had a negligible binding affinity (FIG. 1 B).

As antigen presentation and induction of an effective immune response is critically dependent on MHC haplotype, binding affinities of K27M$_{26-35}$ to the most frequent class I haplotypes were analyzed. A relevant and mutation-specific binding was predicted especially for HLA-A*02 (FIG. 1 C). Indeed, vaccination of HLA-A2* mice with the predicted 10mer K27M$_{26-35}$ induced IFNγ$^+$CD8$^+$-driven mutation-specific cytotoxic T-cell responses shown by intracellular flow cytometry (FIG. 1 D). Additionally, K27M$_{26-35}$-specific CD8$^+$ T-cells could be detected directly using a HLA-A2* dextramer (FIG. 1 E). Thus, anti-tumor efficacy of H3.3 K27M peptide vaccination was further investigated in a syngeneic HLA-A*02 tumor model.

Figure 2:
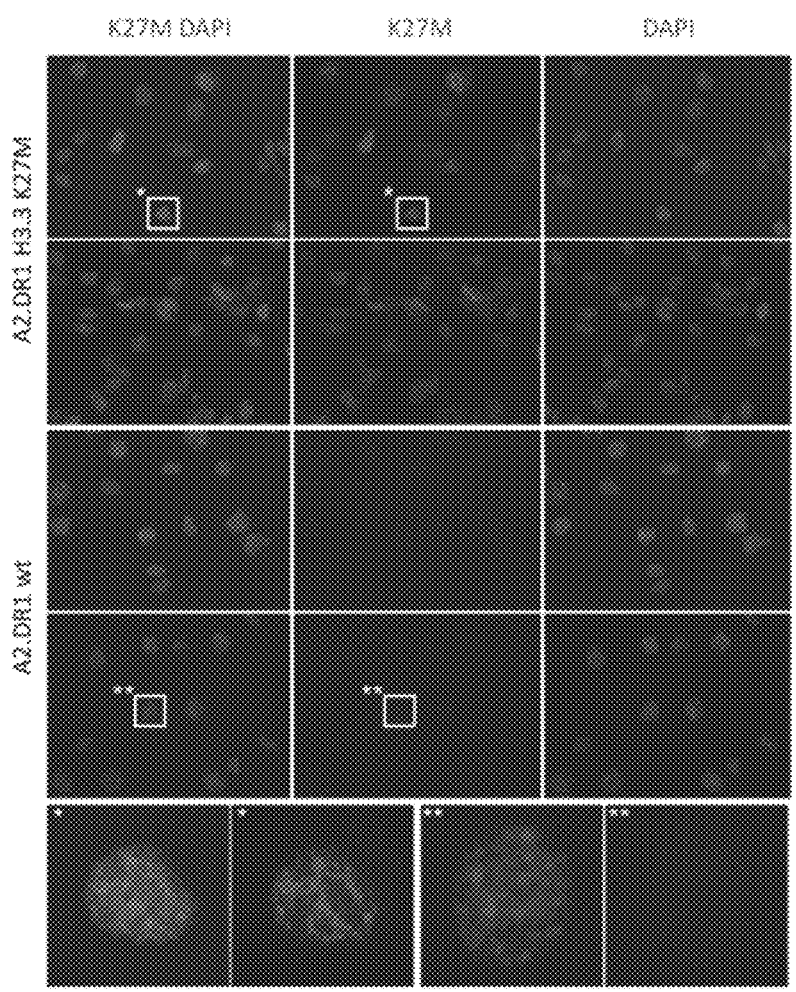
FIG. 2: (A) Generation of H3.3 K27M expressing A2.DR1 sarcoma cells: H3.3 K27M expression in transduced A2.DR1 sarcoma cells or wildtype cells by immunofluorescent staining using a mutation-specific antibody. (B+C) H3.3 K27M peptide vaccination reduces H3.3 K27M$^+$ tumor growth in MHC-humanized mice: Growth of pre-established H3.3K27M over-expressing subcutaneous syngeneic tumors in A2.DR1 mice after peptide vaccination with H3.3 K27M$_{14-40}$ (red) or vehicle control (blue) in Montanide® on days 5 and 14 (arrows) (D) and ELISpots of IFNγ splenocyte responses to H3.3 K27M$_{14-40}$ (black), K27 wt$_{14-40}$ (grey) or MOG$_{35-55}$ (white) after therapeutic vaccination of tumor bearing mice (E). Mean+/−s.e.m. of n=6 mice per group are shown. *p<0.05; **p<0.01.
Figure 2:
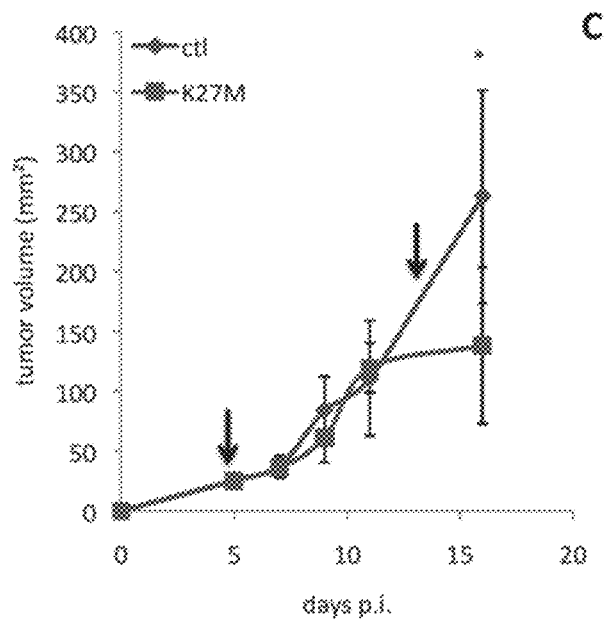
Figure 2:
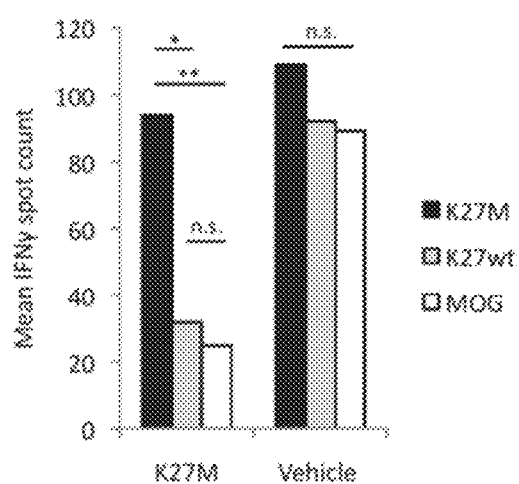

Here, vaccination of tumor bearing A2.DR1 mice with a K27M$_{14}$0.4$_0$ peptide vaccine significantly suppressed the growth of pre-established H3.3 K27M over-expressing A2.DR1 subcutaneous tumors by induction of mutation-specific IFNγ immune responses (FIG. 2).

The invention claimed is:

1. A method of treating a cancer characterized by the expression of the K27M mutated variant of human Histone H3.3 in a subject in need thereof, the method comprising the administration of an effective amount of a peptide comprising the amino acid sequence shown in SEQ ID NO: 13 or an amino acid sequence having a sequence identity of at least 95% to the sequence of SEQ ID NO: 13, wherein the peptide comprises the K27M mutated amino acid position and is not the full length K27M variant of human Histone H3.3.

2. The method according to claim 1, wherein the peptide is capable of eliciting a T cell-mediated immune response in a mammal that is specific for the K27M variant of human Histone H3.3.

3. The method according to claim 1, wherein the peptide consists of (i) the amino acid sequence of SEQ ID NO: 13 (KAPRKQLATKAARMSAPSTGGVKKPHR), or (ii) an amino acid sequence with a sequence identity of at least 95% to the sequence of SEQ ID NO: 13.

4. The method according to claim 1, wherein the peptide is comprised in a fusion protein comprising an amino acid sequence composed of:
   i) the amino acid sequences of at least two peptides, each peptide consisting of the amino acid sequence of SEQ ID NO: 13 (KAPRKQLATKAARMSAPSTGGVKKPHR), or
   ii) the amino acid sequence of SEQ ID NO: 13, and the amino acid sequence of a heat shock protein (HSP) binding domain.

5. The method according to claim 1, wherein the cancer characterized by the expression of the K27M mutated variant of human Histone H3.3 is selected from the group consisting of brain cancer, a cancer of the central nervous system, a glioma, an astrocytoma, and pediatric astrocytoma.

* * * * *